United States Patent [19]

Smyth et al.

[11] 4,120,729

[45] Oct. 17, 1978

[54] NOVEL LOW TEMPERATURE MATURING DENTAL GLAZE

[75] Inventors: Milagros B. Smyth, East Brunswick Township, Middlesex County; James Lee-You, East Windsor Township, Mercer County, both f, N.J.

[73] Assignee: Johnson & Johnson, New Brunswick, N.J.

[21] Appl. No.: 846,050

[22] Filed: Oct. 27, 1977

[51] Int. Cl.$^2$ .................. A61C 13/02; C03C 5/00; C09K 3/00
[52] U.S. Cl. .......................... 106/35; 32/8; 106/48; 106/54
[58] Field of Search .......... 106/48, 54; 32/8; 106/35

[56] References Cited

U.S. PATENT DOCUMENTS 3,640,738  2/1972  Detweiler .................. 106/54

FOREIGN PATENT DOCUMENTS 1,072,689  6/1967  United Kingdom ............ 106/35

OTHER PUBLICATIONS

Kirk-Othmer, Encyclopedia of Chemical Technology, vol. 6 (1965), "Dental Materials," pp. 796-799.
Parmelee, C. W., "Ceramic Glazes," (1951), pub. by Industrial Publications, Inc., Chicago, pp. 215-216, 220.

*Primary Examiner*—Helen McCarthy

[57] ABSTRACT

The instant invention relates to a novel dental glaze which matures at a temperature of from 1400° to 1600° F, that is, at least 200° lower than the vitrifying temperature of dental porcelain. The chemical composition of this novel glaze may be thusly represented, on a weight basis:

| | |
|---|---|
| $SiO_2$ | 45-52% |
| $B_2O_3$ | 15-20% |
| $Al_2O_3$ | 10-15% |
| $K_2O$ | 3.5-7.5% |
| $Na_2O$ | 12-17% |
| CaO | 0-1% |
| ZnO | 0-1% |
| F | 1-3% |

Preferably the instant novel glaze is further characterized as having an average particle size of 10 ± 4 microns and not more than 1% of the particles having a diameter greater than 30 microns.

4 Claims, No Drawings

NOVEL LOW TEMPERATURE MATURING DENTAL GLAZE

FIELD OF INVENTION

The instant invention relates to a novel dental glaze which matures at a temperature of as low as 1350° F. e.g. from 1400° to 1600° F., that is, at least 200° lower than the vitrifying temperature of dental porcelain. The chemical composition of this novel glaze may be represented thusly, on a weight basis:

| | |
|---|---|
| $SiO_2$ | 45–52% |
| $B_2O_3$ | 15–20% |
| $Al_2O_3$ | 10–15% |
| $K_2O$ | 3.5–7.5% |
| $Na_2O$ | 12–17% |
| $CaO$ | 0–1% |
| $ZnO$ | 0–1% |
| $F$ | 1–3% |

To provide easy dispersibility, preferably the instant novel glaze will have an average particle size of $10 \pm 4$ microns and not more than 1% of the particles having a diameter greater than 30 microns.

BACKGROUND OF THE PRIOR ART

Artificial teeth may be fashioned from porcelain which is baked onto a metal substrate. The metal substrate is subsequently used for anchoring the artificial teeth in the person's mouth either on a temporary or permanent basis. The goal of the dental technician is to provide as realistic looking an artificial tooth as possible and therefore the technology involved in this branch of the dental art relates to the appearance of the tooth. Of course, the dental technician must also consider the functional nature of the tooth, i.e. as a chewing or biting surface.

The metal substrate such as a noble metal, i.e. gold; or a non precious metal, i.e. the various nickel and chromium containing alloys which have been recently introduced to the market; is treated to prepare the surface for the coating of the porcelain thereon. The gold substrate may be partially oxidized, for example, to make it easier to bond porcelain thereto. The non noble metal alloys may be treated with a bonding agent, e.g. a dispersion of aluminum and boron powder in a vehicle such as propylene glycol, to prepare the surface for bonding to the porcelain.

The dental technician, after preparing the metal surface, will paint a dispersion of *p-o-p* (paint opaque) porcelain onto the metal and may fire the dispersion coated metal by heating over a temperature of from 1200° F. to 1700° F. in vacuum, at a rate increase of 90° to 100° F. per minute. After a temperature of 1700° F. is reached the vacuum may be broken and the coated metal substrate heated in air at the same temperature rate increase up to 1900° F. The p-o-p porcelain is opaque and hides the metal surface of the artificial tooth completely.

This first porcelain coating is followed by a second coating of a more translucent porcelain known as gingival porcelain. The gingival porcelain is also painted as a dispersion onto the previously fired, porcelain coated metal substrate but before firing a third porcelain known as the incisal porcelain is used to coat that portion of the coated substrate which will form the incisal surface of the artificial tooth. The incisal porcelain is even more translucent than the gingival procelain, thus assuring the realistic look of the artificial tooth. Both the gingival and incisal porcelain may have coloring agents added to match the color of the natural teeth of the person who is to use the artificial tooth or teeth. The incisal porcelain will generally be coated from the incisal edge approximately a third of the way up toward the gingival surface.

After the gingival and incisal porcelain are coated onto the p-o-p porcelain coated metal substrate the tooth is fired in a manner similar to that of the p-o-p porcelain.

If the dental technician has been completely accurate the artificial tooth may be ready at this point for the wearer, however, it generally requies further treatment to fit and look presentable. The dental technician may, for example, have to grind down portions of the tooth so that it will fit more correctly into the mouth of the wearer. The grinding of course, removes any glossy appearance from the surface of the artificial tooth, therefore, a further coating of gingival and/or incisal porcelain, from a dispersion, will be required and the further coated tooth will be fired in a manner similar to the above. As can be appreciated there may be many such further coatings and refirings. Generally, the dental technician, if proficient in his skill, will take approximately three such grindings, coatings and refirings to prepare the artificial tooth. However, up to seven is not uncommon, especially when the dental technician is not of the highest skill.

It is known in the art of ceramics that there is a vitrification point in which the ceramic material has its greatest density. From the standpoint of strength, it is desirable that the material be at the vitrification point. Generally, dental ceramics such as the porcelain described above, vitrify at about 1800° to 1850° F. Therefore, it is evident why the above temperature-time cycle is used to prepare the artificial tooth. It has been found, however, that if you refire many times the vitrification point will be exceeded and it will be found that the ceramic is no longer at its greatest density. The dental technician may notice that the structure will slump after repeated firings thus changing both the shape and the strength of the artificial tooth. Repeated firings also may give rise to an additional problem known as 'checking'. The artificial tooth becomes crazed with spider weblike cracks, again detracting from a natural appearance.

It is also known in the ceramic art, especially the dental ceramic art, that the surface area of the artificial tooth should be somewhat glossy to resemble the appearance of a natural tooth. The above dental ceramics are somewhat glossy after heating to temperatures of about 1800° F. and above, that is they are self glazing when heated to 1800° F. Therefore, subsequent grindings remove the glossy surface and require reheating the artificial tooth to temperatures of at least 1800° F. to restore the gloss. Repeated heatings, of course, as noted above, cause the tooth to pass the vitrification point and then it is no longer suited for its intended end use.

It will thus be clear that repeated coating, grinding and refiring may result in having artificial teeth that are no longer suitable for their end use.

Various products have been put onto the market which are touted as useful for glazing artificial teeth. These products claim to allow the dental technician to heat to a lower temperature after grinding the tooth and obtain a glazed, naturally looking surface. The obvious advantage to products of this kind is evident, in that the dental technician would not have to take the risk of heating the artificial tooth to a point where it is self glazing and thus risk exceeding the vitrification point. It has been found, however, that the glazes on the market mature, that is, form the glossy surface, at temperatures starting at about 1700° F. up to and including 1800° F. Thus to obtain the optimal properties of these glazes the dental technician has to heat to temperatures as high as the temperature at which the dental porcelain is self glazing. To avoid the risk of slumping and checking, the dental technician usually underfires the artificial tooth coated with these prior art glazes, that is, he may heat to a temperature of no more than 1700° F. At this temperature, although he may improve the surface appearance of the artificial tooth as compared to a ground surface, he will not achieve an appearance equivalent to a self glazed ceramic or a natural tooth. Usually a somewhat gritty surface is obtained if the glaze is underfired. Therefore, the use of the prior art glazes represent, at best, a compromise. A dental ceramic glaze which matures at a lower temperature thus would be very valuable to the dental technician.

Various glazes which are purported to mature at a low temperature have been reported in the literature. See, for example, Bulletin, "Dental Porcelain" No. 118 of the Ohio State University Engineering Experiment Station, March 1944. The glazes disclosed therein differ from the instant novel glazes in chemical composition. Moreover, there is no teaching of a preferred average particle size limitation which enables the dental technician to prepare dispersions which are easily painted onto porcelain, coated metal substrate.

SUMMARY OF THE INVENTION

It has now unexpectedly been discovered that a glass which has a representative chemical composition, on a weight basis, as follows:

|  | Broad Range | Preferable Range |
| --- | --- | --- |
| $SiO_2$ | 45–52% | 48.5–50.6 |
| $B_2O_3$ | 15–20% | 16.9–17.9 |
| $Al_2O_3$ | 10–15% | 10.0–12.0 |
| $K_2O$ | 3.5–7.5% | 4.8–5.1 |
| $Na_2O$ | 12–17% | 13.2–13.6 |
| CaO | 0–1% | 0.8–1.0 |
| ZnO | 0–1% | 0.8–1.0 |
| F | 1–3% | 0.7–1.2 | and is characterized as being in the form of a finely divided powder wherein 100% of said powder passes through a 400 mesh screen may be used as a low temperature dental glaze. This novel composition, when used as a dental glaze, matures at a temperature of from 1400° to 1600° F., that is, at least about 200° F. lower than the vitrifying temperature of dental porcelain. The dental glaze of this invention may be prepared by melting together sufficient precursor components to yield the above composition. Suitable precursors for the above include $SiO_2$, $H_3BO_3$, Feldspar, $CaCO_3$, $CaF_2$, ZnO, etc. The preparation of glasses such as the above is well known in the art, for example, −200 mesh powders of the above precursors may be mixed in a blender and heated to a temperature of at least 1800° F. e.g. about 2000° F. in a crucible to form the glass. The molten glass may then be quenched in water, dried and ground in a ball mill, to provide the above composition in the form of a powder. If the powder has not been ground to the preferred average particle size, then the final step in preparing the novel glaze of the instant invention is separating the coarse particles from the particles which are fine enough to pass through a 400 mesh screen. It has been found that a glass having the above chemical composition, when provided in a particle size wherein 100% passes through the 400 mesh screen, yields a product which is easily dispersed and the resulting dispersion has excellent paintability, e.g. the viscosity and settling rate is suitable for the dental technician's use. It has been found that coarser particle size dispersions are more apt to be applied less uniformly to the porcelain coated metal substrate, creating a streaked or uneven appearance after firing. The instant novel glaze has a preferred average particle size when measured by the Coulter Counter of from 8 to 11 microns and not more than 1% of the particles are greater than 30 microns. In general, screening through the 400 mesh screen is necessary to obtain this average particle size, however, other methods may be used to prepare the instant novel glaze compositions, e.g. the powder may be wet ground in ball mill utilizing water to disperse and lubricate the ground particles.

The novel glaze described and claimed herein is also characterized as having an excellent coefficient of expansion. More particularly, the novel glaze will have a coefficient of thermal expansion of from $9 \times 10^{-6}$ to $12 \times 10^{-6}$, which is lower than most dental porcelains which are about $13 \times 10^{-6}$ in/in/° C.

This difference in thermal expansion puts the surface into compression therefore, increasing the tensile strength of the surface. It should be noted that the glazes taught in the above Bulletin are not described as having this property.

The translucency of the instant novel glaze allows the coloring of the porcelain formulations to show through without alteration from the glaze itself. Moreover, due to its inert nature, the instant novel glaze does not react with the pigments present in the porcelain at the conditions of application or use.

Furthermore, it has been found that the glaze does not interfere with the fluorescence of the dental porcelains available in the art. This is important since natural teeth fluoresce in black light and therefore fluorescence in an artifical tooth is desirable.

The following are specific examples of the instant invention. There is no intent, however, to be bound to the specific embodiment disclosed herein. It should be noted that unless otherwise stated all firings were commenced at 1200° F. in vacuum and the temperature increased at a rate of from 90° to 100° F. per minute up to the temperature noted.

EXAMPLE 1

A mixture of powders all of which pass through a 200 mesh screen are weighed to give a product having the chemical composition within the limits:

| $SiO_2$ | 49.7 |
| --- | --- |
| $B_2O_3$ | 16.9 |
| $Al_2O_3$ | 12.1 |
| $K_2O$ | 5.4 |
| $Na_2O$ | 14.7 |
| CaO | 0.5 |
| ZnO | 0.7 |
| F | 1.8 |

The precursor compounds include $SiO_2$, $H_3BO_3$; $CaCO_3$ Feldspar, Calcium Fluoride and ZnO.

After blending, the mixture is heated in a crucible to a temperature of at least 1800° F., quenched in water, dried and ground in a ball mill. After grinding the mixture is seived and a material retained by a 400 mesh screen is discarded.

EXAMPLE 2

The firing characteristic of the glaze was studied from the onset of glazing at 1400° F. to the very shiny glossy finish obtained at 1650° F. The results are tabulated as follows:

| Temperature (° F) | Time of Soak (Min) | Kind of Finish |
|---|---|---|
| 1400 | — | matte |
| 1400 | 2 | matte |
| 1400 | 5 | matte |
| 1450 | — | slightly glossy matte |
| 1450 | 5 | slightly glossy textured |
| 1500 | — | slightly glossy textured |
| 1500 | 2 | slightly glossy textured |
| 1500 | 5 | glossy slightly textured (like natural teeth) |
| 1550 | — | glossy textured |
| 1600 | — | glossy slightly textured |
| 1650 | — | very glossy and smooth |

*held at the noted temperature.

The best finish according to visual examination is obtained at 1500° F. after soaking for 5 minutes or 1600° F. with no soaking. Some dental laboratories might prefer also the 1650° F. with no soak which gives a very nice glossy and smooth finish.

EXAMPLE 3

Comparison of the Instant Novel Glaze With Commercial Glazes

The glaze compositions below were tested on porcelain crowns and compared. As will be seen from the table below better glazing properties are obtained with the instant novel glaze.

TABLE I

| Glaze | Firing Temperatures | Comments* |
|---|---|---|
| A (The Glaze of Example I) | 1350–1650° F | Flowed more evenly during firing and had a smooth surface to the touch |
| B (Steele Super Glaze)** | 1760–1945° F | Surface not equal to Glaze A |
| C (CERAMCO Glaze available from CERAMCO, Inc. 31-16 Hunter's Point Avenue, Long Island City, N.Y.) | 1600–1800° F | Surface was gritty |

**This sample has the following compositions:

| | | | |
|---|---|---|---|
| $SiO_2$ | Silicon dioxide | 67.19 | % |
| $Al_2O_3$ | Aluminum oxide | 4.99 | |
| $Fe_2O_3$ | Iron oxide | 0.050 | |
| PbO | Lead oxide | 0.01 | |
| ZnO | Zinc oxide | 1.05 | |
| CaO | Calcium oxide | 5.20 | |
| BaO | Barium oxide | 2.18 | |
| MgO | Magnesium oxide | 0.35 | |
| $Na_2O$ | Sodium oxide | 5.81 | |
| $K_2O$ | Potassium oxide | 2.63 | |
| $B_2O_3$ | Boric oxide | 10.36 | |
| $F_2$ | Fluorine | 0.08 | |
| | | 99.86 | % |

It is noted that the instant novel glaze had the best properties when compared to two commercial products. It is also noted that these properties were achieved at temperatures which were up to 200° lower than used to prepare the other glazed products.

EXAMPLE 4

Evaluation of Firing Rate of the Instant Novel Glaze

The firing range of the instant novel ceramic glaze, as with other glazes, depends on the firing rate. A normal porcelain firing rate as noted above would be a temperature increase of from 90° to 100° F. per minute. At this rate the instant novel glaze has a firing range of 1500° to 1600° F. It should also be noted that thicker coats achieve a greater degree of maturity for a given temperature than thin coats.

Experimental Procedure — Prefired disks of CERAMCO Gingival Porcelain three-fourths inch in diameter were ground on one side with 80 grit silicone carbide paper. The instant novel glaze was mixed with a liquid medium, i.e. propylene glycol, in a ratio of two parts powder and one part liquid to form a paste having a paintable consistency. The glaze paste was brushed on an area approximately three-fourths of an inch in diameter in the center of each disk. Each sample was fired by starting at a temperature of about 1200° F. and increasing the temperature at the variable rate given below. The samples were observed for start of fusion, start of glaze maturation and end of glaze maturation. The start of maturation for purposes of this patent application is defined to mean the first appearance of a glassy sheen and the end of maturation is the temperature at which the glaze reaches a completely glassy smooth surface. See Table II below for the results.

TABLE II

| | Firing Rate | | |
|---|---|---|---|
| | 90–100 ° F/min. | 50–60 ° F/min. | 35–40 ° F/min. |
| Start of Fusion | 1450° F | 1400° F | 1350° F |
| State of Glaze Maturation | 1500° F | 1450° F | 1400° F |
| End of Glaze Maturation | 1600° F | 1550° F | 1500° F |

The more rapid firing rate of 90° to 100° F. per minute is generally preferred by dental technicians, however, a very low maturing temperature can be achieved with the instant novel glaze if the rate is lowered to 35° to 40° F. per minute

EXAMPLE 5

Thermal Expansion of the Instant Novel Glaze As noted above, it is important that the glaze have a thermal expansion which is lower than that of the porcelain coated metal substrate structure so that it will be put into compression. Otherwise temperature changes during firing may cause checking in the artificial tooth. As noted below, the coefficient of expansion is measured by means of Differential Dilatometry.

Differential Dilatometry is based upon the principle that solids usually expand when heated. With this method, the change in length of a test bar of fixed initial length is compared to the change in length of a fused silica standard of the same fixed initial length when both are heated side by side in the dilatometer assembly from room temperature to 500° C.

The results are recorded in Table III below. Note that sample A is similar in composition and average particle size to the sample prepared in Example I.

TABLE III

| Specimen | Coef. of Thermal Expansion in/in/° C over the range of (25–450° C) |
|---|---|
| A | $9.106 \times 10^{-6}$ |

EXAMPLE IV

Particle Size Distribution

A sample prepared by the method of Experiment I has an average particle size of 19-20 $\mu$ and from 20 to 30% greater than 30 $\mu$ as measured by the Coulter Counter Model TA 11. available from Coulter Diagnostics, Inc., Hialeah, Fla. This is Sample A. A portion of Sample A is screened through a 400 mesh screen and the average particle size is from 8.0 to 11.0 $\mu$ and not more than 1% greater than 30$\mu$. This is Sample B. Dispersions of 1 part of each of the aforesaid samples and 2 parts propylene glycol are prepared. The dispersion of Sample B is found to paint more uniformly on to a porcelain coated metal substrate. After firing, at a temperature rate increase of from 90° to 100° F. to a temperature of 1600° F., the substrate painted with Sample B was found to have a smooth glossy appearance while the substrate painted with Example A was streaked and uneven due to the difficulty in applying this coarser particle size dispersion uniformly.

What is claimed is:

1. A translucent dental glaze composition suitable for application to a dental porcelain coated metal substrate, said glaze having (a) an average particle size of 10 ± 4 microns and not more than 1% of the particles having a diameter greater than 30 microns, (b) a maturing temperature of from 1400° to 1600° F. and at least about 200° F. lower than the vitrifying temperature of the dental porcelain of the substrate, and (c) a coefficient of thermal expansion of from 9 to 12 $\times 10^{-6}$/° C. which is lower than the coefficient of thermal expansion of the dental porcelain, and consisting essentially of, on a weight basis:

| | |
|---|---|
| $SiO_2$ | 45–52% |
| $B_2O_3$ | 15–20% |
| $Al_2O_3$ | 10–15% |
| $K_2O$ | 3.5–7.5% |
| $Na_2O$ | 12–17% |
| CaO | 0–1% |
| ZnO | 0–1% |
| F | 1–3% |

2. The glaze of claim 1 consisting essentially of, on a weight basis:

| | |
|---|---|
| $SiO_2$ | 48.5 – 50.6 |
| $B_2O_3$ | 16.9 – 17.9 |
| $Al_2O_3$ | 10.0 – 12.0 |
| $K_2O$ | 4.8 – 5.1 |
| $Na_2O$ | 13.2 – 13.6 |
| CaO | 0.8 – 1.0 |
| ZnO | 0.8 – 1.0 |
| F | 0.7 – 1.2 |

3. The glaze of claim 2 having a coefficient of thermal expansion of about $9.1 \times 10^{-6}$.

4. In a method for glazing an artificial tooth comprising a dental porcelain coated metal substrate which has been previously fired and ground comprising the steps of coating said tooth with a dispersion of a glaze in a liquid vehicle, drying said tooth to remove said liquid, and firing said dried tooth, the improvement whereby the tooth is fired to a glossy, slightly textured finish at a temperature of from 1400° to 1600° F. and the glaze is a composition according to claim 1.

* * * * *

UNITED STATES PATENT AND TRADEMARK OFFICE
CERTIFICATE OF CORRECTION

PATENT NO. : 4,120,729
DATED : October 17, 1978
INVENTOR(S) : Milagros B. Smyth and James Lee-You It is certified that error appears in the above-identified patent and that said Letters Patent are hereby corrected as shown below:

On the face page, Inventors:, "both f, N.J." should read
---both of N.J.---
In Column 2, line 12, "requies" should read ---requires---
In Column 5, Example 2, in the table, "Time of Soak" should read
---Time of Soak*---
In Column 5, line 50, Table I, "This sample has the following compositions:" should read ---This sample has the following composition:---
In Column 6, line 19, "three-fourths" should read ---three-eighths---
In Column 7, line 5, Thermal Expansion of the Instant Novel Glaze should read as title of EXAMPLE 5

Signed and Sealed this

Twentieth Day of March 1979

[SEAL]

Attest:

RUTH C. MASON
Attesting Officer

DONALD W. BANNER
Commissioner of Patents and Trademarks